United States Patent [19]
Kumar

[11] Patent Number: 5,552,091
[45] Date of Patent: Sep. 3, 1996

[54] BENZOPYRAN COMPOUNDS

[75] Inventor: Anil Kumar, Pittsburgh, Pa.

[73] Assignee: PPG Industries, Inc., Pittsburgh, Pa.

[21] Appl. No.: 497,516

[22] Filed: Jun. 30, 1995

Related U.S. Application Data

[63] Continuation-in-part of Ser. No. 220,344, Mar. 30, 1994, Pat. No. 5,429,774, which is a continuation-in-part of Ser. No. 201,948, Feb. 25, 1994, abandoned, which is a continuation-in-part of Ser. No. 30,932, Mar. 12, 1993, abandoned.

[51] Int. Cl.$^6$ ............ G02B 5/23; C07D 209/82; C07D 333/50; C07D 311/78
[52] U.S. Cl. ............ 252/586; 549/42; 549/383; 549/389; 549/457; 548/440
[58] Field of Search ............ 252/586; 549/42, 549/383, 389, 457; 548/440

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 4,215,010 | 7/1980 | Hovey et al. | 252/300 |
| 4,342,668 | 8/1982 | Hovey et al. | 252/586 |
| 4,637,698 | 1/1987 | Kwak et al. | 351/163 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 4,880,667 | 11/1989 | Welch | 427/160 |
| 4,931,219 | 6/1990 | Kwiatkowski et al. | 252/160 |
| 4,990,287 | 2/1991 | Bennion et al. | 252/586 |
| 5,066,818 | 11/1991 | Gemert et al. | 549/389 |
| 5,200,116 | 4/1993 | Heller | 252/586 |
| 5,238,981 | 8/1993 | Knowles | 549/389 |
| 5,244,602 | 9/1993 | VanGemert | 252/586 |
| 5,274,132 | 12/1993 | VanGemert | 549/389 |
| 5,384,077 | 1/1995 | Knowles | 252/586 |
| 5,405,958 | 4/1985 | VanGemert | 544/71 |
| 5,411,679 | 5/1995 | Kumar | 252/586 |
| 5,429,774 | 7/1995 | Kumar | 252/586 |

FOREIGN PATENT DOCUMENTS

| | | |
|---|---|---|
| 62-195383 | 8/1987 | Japan . |
| 7-41758 | 2/1995 | Japan . |
| 7-48363 | 2/1995 | Japan . |
| 7-48566 | 2/1995 | Japan . |
| 7-48567 | 2/1995 | Japan . |

OTHER PUBLICATIONS

*Friedel–Crafts and Related Reactions*, George A. Olah, Interscience Publishers, vol. 3 Chapter XXXI, pp. 1–8, 1964.
"Regioselective Friedel Crafts Acylation of 1,2,3,4–Tetrahydroquinoline and Related Nitrogen Heterocycles: Effects of NH Protective Groups and Ring Size", Ishihara, Y., et al., J. Chem. Soc., Perkin Trans. 1, pp. 3401–3406, 1992.
*Heterocyclic Compounds*, R. C. Elderfield, 1951, vol. 2, Chapters 3 and 5, pp. 123–144, pp. 164–174.
*The Chemistry of Heterocyclic Compounds*, H. D. Hartough et al., 1954, vol. 7, Chapter IV, pp. 225–282.
*Advances in Heterocyclic Chemistry*, A. R. Katritzky et al., 1974, vol. 16, Chapter V.
Akermark et al., Acta Chemica Scandinavica, vol. 13, 1959, pp. 1855–1862.
S. Granowitz et al., Acta Pharm. Suec., vol. 15, 1978, pp. 337–360.
J.A.C.S. vol. 61, Apr. 1939, pp. 951–956; Dibenzofuran. IX Metalation of Some Derivatives.
J.A.C.S. vol. 87 (2), 1965, pp. 213–217; The Electron Spin Resonance Spectra of the Dibenzothiophene Radical Anion and Its Isologs and the Electronic Structure of Conjugated Sulfur–Containing Heterocycles.
J.A.C.S. vol. 62, Mar. 1940, pp. 667–669. Dibenzofuran. XVIII. Isomeric Metalation Products of Some Phenols and Their Methyl Ethers.

*Primary Examiner*—Philip Tucker
*Attorney, Agent, or Firm*—Frank P. Mallak; Irwin M. Stein

[57] ABSTRACT

Described are novel reversible photochromic benzopyran compounds, examples of which are compounds substituted at the 2-position of the pyran ring with a dibenzo-fused 5 member heterocyclic compound; other enumerated substituents at the other 2-position of the pyran ring; and a substituted or unsubstituted benzo, benzothieno or benzofurano group fused to the benzo portion of the benzopyran. Also described are organic host materials that contain or that are coated with such compounds. Articles such as ophthalmic lenses or other plastic transparencies that incorporate the novel benzopyran compounds or combinations thereof with complementary photochromic compounds, e.g., spiro(indoline) type compounds, are also described.

20 Claims, No Drawings

BENZOPYRAN COMPOUNDS

This application is a continuation-in-part of Application Ser. No. 08/220,344, filed Mar. 30, 1994, now U.S. Pat. No. 5,429,774, which is a continuation-in-part of abandoned Application Ser. No. 8/201,948, filed Feb. 25, 1994, which is a continuation-in-part of abandoned Application Ser. No. 08/030,932, filed Mar. 12, 1993.

DESCRIPTION OF THE INVENTION

The present invention relates to certain novel benzopyran compounds. More particularly, this invention relates to novel photochromic benzopyran compounds and to compositions and articles containing such novel benzopyran compounds. When exposed to light radiation involving ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

The present invention relates to novel benzopyran compounds which exhibit color changes from colorless to colors ranging from yellow to red/purple. These compounds are substituted at the 2-position of the pyran ring with a dibenzo-fused 5 member heterocyclic compound; other enumerated substituents at the other 2-position of the pyran ring; and a substituted or unsubstituted benzo, benzothieno or benzofurano group fused to the benzo portion of the benzopyran.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

In accordance with the present invention, it has now been discovered that certain novel benzopyran compounds having a high activated intensity and high coloration rate may be prepared. These compounds may be described as benzopyrans substituted at the 2-position of the pyran ring with a dibenzo-fused 5 member heterocyclic compound; other substituents at the other 2-position of the pyran ring; and a substituted or unsubstituted benzo, benzothieno, or benzofurano group fused to the benzo portion of the benzopyran, the 2,3 position or 3,2 position of the benzothieno or benzofurano group being fused to the f, g, or h side of the benzopyran compound, and the benzo group being fused to the f side of the benzopyran. These benzopyran compounds may be represented by the following graphic formula:

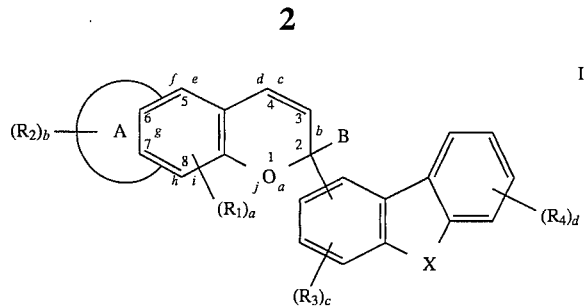

In graphic formula I, X may be $CH_2$, O, i.e., oxygen, S, i.e., sulfur, or $N-R_{12}$, wherein $R_{12}$ is selected from the group consisting of hydrogen, $C_1-C_6$ alkyl, e.g., methyl, ethyl, propyl, butyl, pentyl, and hexyl, $C_5-C_7$ cycloalkyl, unsubstituted, mono- and di-substituted phenyl, the phenyl substituents being $C_1-C_6$ alkyl, $C_1-C_6$ alkoxy, chloro, or fluoro, $R_3$ and $R_4$ are each, i.e., each $R_3$ and each $R_4$, hydrogen, $C_1-C_6$ alkyl, $C_1-C_6$ alkoxy, chloro or fluoro, and c and d are each the integers 0, 1, 2, or 3.

Preferably, X is O, S, or $N-R_{12}$, wherein $R_{12}$ is selected from the group consisting of hydrogen, $C_1-C_4$ alkyl, $C_5-C_7$ cycloalkyl, unsubstituted, mono- and di-substituted phenyl, said phenyl substituents being $C_1-C_4$ alkyl, $C_1-C_4$ alkoxy, chloro, or fluoro, $R_3$ and $R_4$ are each hydrogen, $C_1-C_4$ alkyl, $C_1-C_4$ alkoxy, chloro or fluoro, and c and d are each 0, 1, 2, or 3.

More preferably, X is O, S, or $N-R_{12}$, wherein $R_{12}$ is $C_1-C_4$ alkyl, $R_3$ and $R_4$ are each hydrogen, $C_1-C_3$ alkyl, $C_1-C_3$ alkoxy, or fluoro, and c and d are each 0, 1 or 2.

Most preferably, X is O, S, or $N-R_{12}$, wherein $R_{12}$ is $C_1-C_2$ alkyl, $R_3$ and $R_4$ are each hydrogen, $C_1-C_2$ alkyl, $C_1-C_2$ alkoxy, or fluoro, and c and d are each 0 or 1.

Each $R_1$ in graphic formula I may be selected from the group consisting of halogen, $C_1-C_6$ alkyl, $C_3-C_7$ cycloalkyl, the unsubstituted, mono-, and di-substituted aryl groups phenyl and naphthyl, and the groups, $-C(O)W$, $-N(R_5)R_6$, and $-OR_7$, wherein W is hydrogen, $C_1-C_6$ alkoxy, or $-N(R_5)R_6$, $R_5$ and $R_6$ are each selected from the group consisting of hydrogen, $C_1-C_6$ alkyl, $C_5-C_7$ cycloalkyl, unsubstituted, mono- and di-substituted phenyl, or $R_5$ and $R_6$ together with the nitrogen atom form an unsubstituted, mono-, or di-substituted heterocyclic ring selected from the group consisting of 1-indolinyl, morpholino, piperidino, and 1-pyrrolidyl, $R_7$ is hydrogen, $C_1-C_6$ alkyl, unsubstituted or mono-substituted phenyl($C_1-C_3$)alkyl, $C_1-C_6$ alkoxy($C_2-C_4$)alkyl, $C_3-C_7$ cycloalkyl, mono ($C_1-C_4$) alkyl substituted ($C_3-C_7$) cycloalkyl, $C_1-C_6$ haloalkyl, allyl, or the group, $-C(O)Y$, wherein Y is $C_1-C_6$ alkyl, $C_1-C_6$ alkoxy, the unsubstituted, mono-, or di-substituted aryl groups phenyl or naphthyl, an unsubstituted, mono-, or di-substituted phenoxy, $C_1-C_6$ alkylamino, an unsubstituted, mono-, or di-substituted phenylamino, each of said heterocyclic, phenyl, naphthyl, phenyl($C_1-C_3$)alkyl, phenoxy, and phenylamino substituents being $C_1-C_6$ alkyl or $C_1-C_6$ alkoxy, each of said halogen or halo substituents being chloro or fluoro, and a is the integer 0, 1, or 2.

Preferably, each $R_1$ is selected from the group consisting of fluoro, $C_1-C_4$ alkyl, $C_5-C_7$ cycloalkyl, unsubstituted, mono-, and di-substituted phenyl, the groups $-C(O)W$, $-N(R_5)R_6$, and $-OR_7$, wherein W is hydrogen, $C_1-C_4$ alkoxy, or $-N(R_5)R_6$, $R_5$ and $R_6$ are each selected from the group consisting of hydrogen, $C_1-C_4$ alkyl, $C_5-C_7$ cycloalkyl, unsubstituted, and mono-substituted phenyl, or $R_5$ and $R_6$ together with the nitrogen atom form an unsubstituted or mono-substituted heterocyclic ring selected from the group consisting of 1-indolinyl, morpholino, piperidino, and 1-pyrrolidyl, $R_7$ is hydrogen, $C_1$–$C_4$ alkyl, an unsubstituted or mono-substituted phenyl($C_1$–$C_2$)alkyl, $C_1$–$C_4$ alkoxy($C_2$–$C_4$)alkyl, $C_5$–$C_7$ cycloalkyl, mono($C_1$–$C_2$)alkyl substituted ($C_3$–$C_7$) cycloalkyl, $C_1$–$C_4$ haloalkyl, allyl, or the group, —C(O)Y, wherein Y is $C_1$–$C_4$ alkyl or $C_1$–$C_4$ alkoxy, said heterocyclic, phenyl and phenyl($C_1$–$C_2$)alkyl substituents being $C_1$–$C_4$ alkyl or $C_1$–$C_4$ alkoxy, said halo substituents being chloro or fluoro, and a is 0, 1, or 2.

More preferably, each $R_1$ is selected the group consisting of fluoro, $C_1$–$C_3$ alkyl, phenyl, and the groups —C(O)W, —N($R_5$)$R_6$, and —O$R_7$, wherein W is hydrogen, $C_1$–$C_3$ alkoxy, or —N($R_5$)$R_6$, $R_5$ and $R_6$ each being selected from the group consisting of hydrogen, $C_1$–$C_3$ alkyl, $C_5$–$C_7$ cycloalkyl, unsubstituted, and mono-substituted phenyl, or $R_5$ and $R_6$ form an unsubstituted or mono-substituted heterocyclic ring selected from the group consisting of 1-indolinyl, morpholino, and piperidino, $R_7$ is hydrogen, $C_1$–$C_3$ alkyl, or the group, C(O)Y, wherein Y is $C_1$–$C_3$ alkyl or $C_1$–$C_3$ alkoxy, said phenyl and heterocyclic substituents being $C_1$–$C_2$ alkyl or $C_1$–$C_2$ alkoxy, and a is 0 or 1.

Most preferably, each $R_1$ is $C_1$–$C_2$ alkyl, phenyl, the group —C(O)W, or —O$R_7$, wherein W is hydrogen or $C_1$–$C_2$ alkoxy, $R_7$ is hydrogen or $C_1$–$C_2$ alkyl, or $R_7$ is the group, —C(O)Y, wherein Y is $C_1$–$C_2$ alkyl or $C_1$–$C_2$ alkoxy, and a is 0 or 1.

In graphic formula I, A may be selected from the group consisting of benzothieno, benzofurano, and benzo, the 2,3 or 3,2 position of the benzothieno or benzofurano group being fused to the f, g, or h side of the benzopyran compound, and the benzo group being fused to the f side of the benzopyran compound. Each $R_2$ may be selected from the group consisting of $R_1$, and an unsubstituted, mono-, or di-substituted benzo group fused to the benzo portion of the benzothieno or benzofurano of group A, said benzo substituents being $C_1$–$C_4$ alkyl, $C_1$–$C_4$ alkoxy, $C_5$–$C_7$ cycloalkyl, chloro or fluoro, and b is the integer 0, 1, or 2, provided that when $R_2$ is an unsubstituted, mono-, or di-substituted benzo group, b is 1.

Preferably, A is selected from the group consisting of benzothieno, benzofurano, and benzo, the 2,3 or 3,2 position of the benzothieno or benzofurano group being fused to the f or g side of the benzopyran compound, and the benzo group being fused to the f side of the benzopyran compound. Each $R_2$ is selected from the group consisting of $R_1$, and an unsubstituted, mono-, or di-substituted benzo group fused to the benzo portion of the benzothieno or benzofurano of group A, said benzo substituents being $C_1$–$C_3$ alkyl, $C_1$–$C_3$ alkoxy, $C_5$–$C_6$ cycloalkyl, or fluoro, and b is 0, 1, or 2, provided that when $R_2$ is an unsubstituted, mono-, or di-substituted benzo group, b is 1.

More preferably, A is selected from the group consisting of benzothieno, benzofurano, and benzo, the 2,3 or 3,2 position of said benzothieno or benzofurano group being fused to the f or g side of said benzopyran compound, and the benzo group being fused to the f side of the benzopyran. Each $R_2$ is selected from the group consisting of $R_1$, an unsubstituted, or mono-substituted benzo group fused to the benzo portion of the benzothieno or benzofurano of group A, said benzo substituents being $C_1$–$C_2$ alkyl, $C_1$–$C_2$ alkoxy, or fluoro, and b is 0 or 1, provided that when $R_2$ is an unsubstituted, mono-, or di-substituted benzo group, b is 1.

Most preferably, A is selected from the group consisting of benzothieno, benzofurano, and benzo, the 3,2 position of said benzothieno or benzofurano group being fused to the f or g side of the benzopyran compound, and the benzo group being fused to the f side of the benzopyran. Each $R_2$ is $R_1$ or a benzo group fused to the benzo portion of the benzothieno or benzofurano of group A, and b is 0 or 1, provided that when $R_2$ is an unsubstituted, mono-, or di-substituted benzo group, b is 1.

In graphic formula I, B is selected from the group consisting of:

(i) the unsubstituted, mono-, di-, and tri-substituted aryl groups phenyl and naphthyl;

(ii) the unsubstituted, mono-, and di-substituted heterocyclic aromatic groups pyridyl, furanyl, benzofuran-2-yl, benzofuran-3-yl, thienyl, benzothien-2-yl, and benzothien-3-yl, the phenyl and naphthyl substituents of part (i) and the heterocyclic substituents of part (ii) being selected from the group consisting of —N($R_5$)$R_6$, hydroxy, $C_1$–$C_6$ alkyl, $C_1$–$C_6$ haloalkyl, $C_1$–$C_6$ alkoxy, mono($C_1$–$C_6$)alkoxy($C_1$–$C_4$)alkyl, acryloxy, methacryloxy and halogen, the halogen or (halo) groups being fluoro or chloro;

(iii) the groups represented by the following graphic formulae:

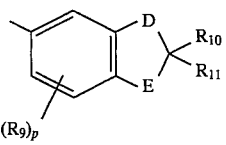
IIA

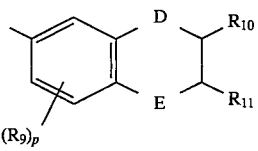
IIB wherein D is carbon or oxygen, and E is oxygen or substituted nitrogen provided that when E is substituted nitrogen, D is carbon, the nitrogen substituents being selected from the group consisting of hydrogen, $C_1$–$C_6$ alkyl, $C_2$–$C_6$ acyl, and $C_1$–$C_5$ alkylcarbonyl; $R_{10}$ and $R_{11}$ are each hydrogen or $C_1$–$C_6$ alkyl; and each $R_9$ is $C_1$–$C_6$ alkyl, $C_1$–$C_6$ alkoxy, hydroxy or halogen, the halogen being chloro or fluoro; and p is the integer 0, 1, or 2;

(iv) $C_1$–$C_6$ alkyl, $C_1$–$C_6$ haloalkyl, ($C_1$–$C_6$) alkoxy($C_1$–$C_4$)alkyl, $C_3$–$C_6$ cycloalkyl, mono($C_1$–$C_6$) alkoxy($C_3$–$C_6$)cycloalkyl, and halo($C_3$–$C_6$)cycloalkyl, each of said halo groups being fluorine or chlorine; and (v) the group represented by the following graphic formula:

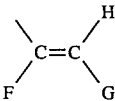
III wherein F is hydrogen or $C_1$–$C_4$ alkyl, and G is selected from the unsubstituted, mono-, and di-substituted members of the group consisting of naphthyl, phenyl, furanyl, and thienyl, said group substituents being $C_1$–$C_4$ alkyl, $C_1$–$C_4$ alkoxy, fluoro, or chloro.

Preferably, B is selected from the group consisting of:

(i) unsubstituted, mono-, di-, and tri-substituted phenyl;

(ii) the unsubstituted, mono- and di-substituted heterocyclic aromatic groups pyridyl, furanyl, benzofuran-2-yl, benzofuran-3-yl, thienyl, benzothien-2-yl, and benzothien-3-yl, the phenyl substituents of part (i) and heterocyclic substituents of this part (ii) being selected from the group consisting of —N($R_5$)$R_6$, hydroxy, $C_1$–$C_4$ alkyl, $C_1$–$C_4$ haloalkyl, $C_1$–$C_4$ alkoxy, and halogen, said halogen or (halo) groups being fluoro or chloro;

(iii) the group represented by graphic formula II A wherein D is carbon and E is oxygen; $R_{10}$ and $R_{11}$ are each hydrogen or $C_1$–$C_4$ alkyl; and each $R_9$ is $C_1$–$C_4$ alkyl, $C_1$–$C_4$ alkoxy, hydroxy or halogen, the halogen being chloro or fluoro; and p is the integer 0, 1, or 2;

(iv) $C_1$–$C_4$ alkyl, $C_1$–$C_6$ alkoxy($C_1$–$C_4$)alkyl, and $C_3$–$C_6$ cycloalkyl; and (v) the group represented by graphic formula III, wherein F is hydrogen or methyl, and G is phenyl or mono-substituted phenyl, the phenyl substituents being $C_1$–$C_4$ alkyl, $C_1$–$C_4$ alkoxy, or fluoro.

More preferably, B is selected from the group consisting of:

(i) unsubstituted, mono-, and di-substituted phenyl;

(ii) the unsubstituted, mono- and di-substituted heterocyclic aromatic groups pyridyl, furanyl, benzofuran-2-yl, thienyl, and benzothien-2-yl, the phenyl substituents of part (i) and heterocyclic substituents of part (ii) being selected from the group consisting of —N($R_5$)$R_6$, hydroxy, $C_1$–$C_3$ alkyl, $C_1$–$C_3$ alkoxy, and fluoro; and (iii) the group represented by graphic formula II A, wherein D is carbon and E is oxygen; $R_{10}$ and $R_{11}$ are each hydrogen or $C_1$–$C_2$ alkyl; each $R_9$ is $C_1$–$C_3$ alkyl, $C_1$–$C_3$ alkoxy, or fluoro; and p is the integer 0, 1, or 2.

Most preferably, B is selected from the group consisting of:

(i) unsubstituted, mono-, and di-substituted phenyl;

(ii) the unsubstituted, mono- and di-substituted heterocyclic aromatic groups pyridyl, furanyl, benzofuran-2-yl, thienyl, and benzothien-2-yl, the phenyl substituent of part (i) and heterocyclic substituents of part (ii) being selected from the group consisting of morpholino, $C_1$–$C_2$ alkyl, $C_1$–$C_2$ alkoxy, and fluoro; and (iii) the group represented by graphic formula II A, wherein D is carbon and E is oxygen; $R_{10}$ and $R_{11}$ are each hydrogen or $C_1$–$C_2$ alkyl; each $R_9$ is $C_1$–$C_2$ alkyl, $C_1$–$C_2$ alkoxy, or fluoro; and p is the integer 0 or 1.

In graphic formula I, like letters used with respect to the definition of different substituents have the same meaning.

Compounds represented by graphic formula I A, i.e., graphic formula I in which B is a substituted phenyl, may be prepared by a coupling reaction of an appropriately substituted or unsubstituted propargyl alcohol (prepared in Reactions A and B) with an appropriately substituted or unsubstituted 2-naphthol, hydroxydibenzothiophene or hydroxydibenzofuran as described in Reaction C. The propargyl alcohol may be prepared as described in Reaction B using the benzoyl derivative of the carbazole, dibenzothiophene or dibenzofuran prepared in Reaction A. The benzoyl derivative of the carbazole, dibenzothiophene or dibenzofuran may be prepared by Friedel-Crafts methods. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992; *Heterocyclic Compounds*, Robert Elderfield, 1951, Vol. 2, Chapter 3 (Dibenzofuran) and Chapter 5 (Dibenzothiophene); *The Chemistry of Heterocyclic Compounds*, H. D. Hartough and S. L. Meisel, 1954, Vol. 7, Chapter IV (Dibenzothiophene and its Derivatives); *Advances in Heterocyclic Chemistry*, A. R. Katritzky and A. J. Boulton, 1974, Vol. 16, Chapter V (Recent Advances in the Chemistry of Dibenzothiophenes); *Heterocyclic Compounds*, Robert C. Elderfield, 1952, Vol. 3, Chapter 3 (The Chemistry of Carbazole).

In Reaction A, the compounds represented by graphic formulae IV and V are dissolved in a solvent, such as carbon disulfide or methylene chloride, in the presence of a Lewis acid, such as aluminum chloride, to form the corresponding substituted ketone represented by graphic formula VI. R represents potential phenyl substituents.

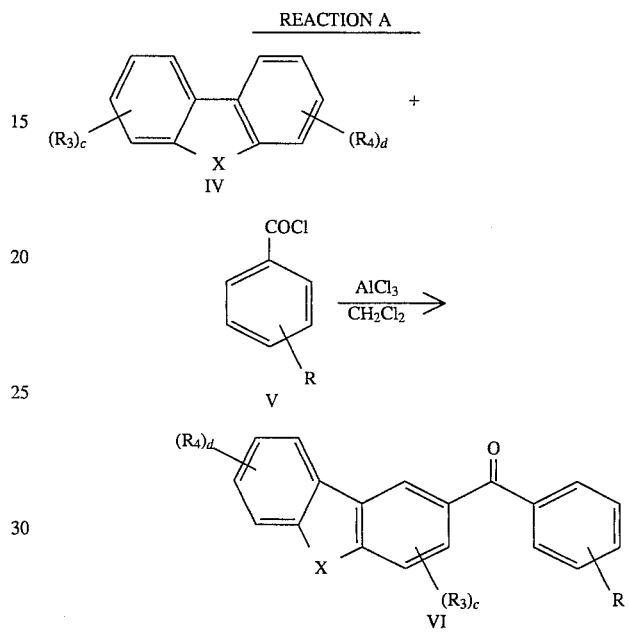

The ketone represented by graphic formula VI in Reaction B is reacted with sodium acetylide in a suitable solvent, such as anhydrous tetrahydrofuran, to form the corresponding propargyl alcohol represented by graphic formula VII.

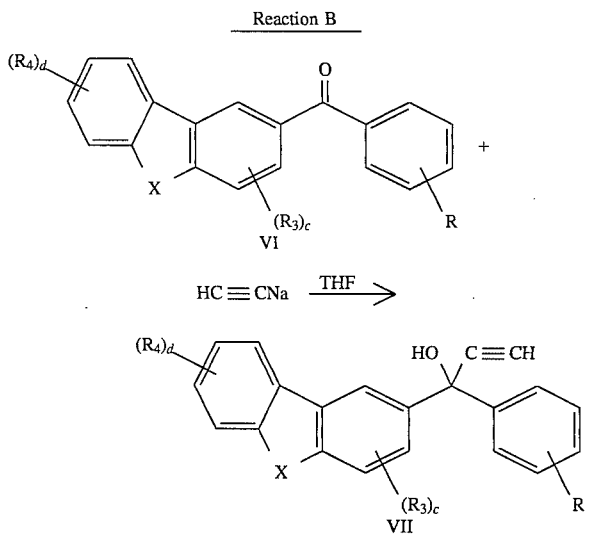

In Reaction C, the propargyl alcohol represented by graphic formula VII is coupled with a substituted or unsubstituted hydroxydibenzofuran, hydroxydibenzothiophene, or 2-naphthol represented by graphic formula VIII, in a solvent such as toluene under acidic conditions, e.g. p-toluenesulfonic acid (p-TsOH), to form the heterocyclic-fused benzopyran or benzo fused benzopyran of graphic formula IA.

Other propargyl alcohols may be used in Reaction C to form compounds of graphic formula I having different substituents at the 2 position of the pyran ring.

graphic formula I C may be produced in addition to a major amount, i.e., from about 60 to about 95 weight percent of the total product, of isomer represented by graphic formula I B

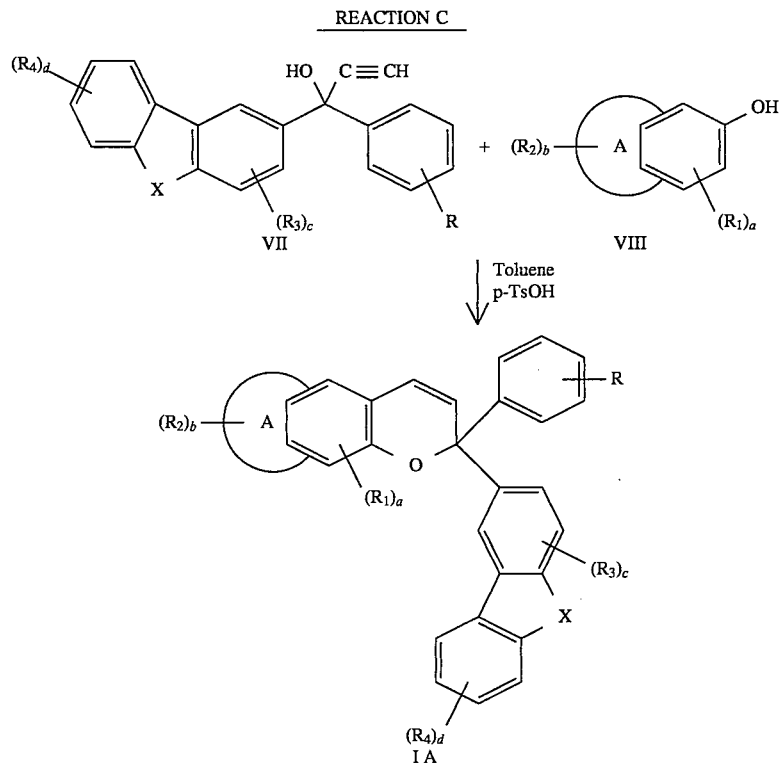

As shown in Reaction D, when either 2-hydroxydibenzofuran or 2-hydroxydibenzothiophene, represented by graphic formula VIII A, (wherein Y is oxygen or sulfur), is coupled with the propargyl alcohol represented by graphic formula VII, a minor amount, i.e., from about 5 to about 40 weight percent of the total product, of isomer represented by as shown in Reaction D. A similar outcome would also result when either 3-hydroxydibenzofuran or 3-hydroxydibenzothiophene is used in place of the compound represented by graphic formula VIII A in Reaction D.

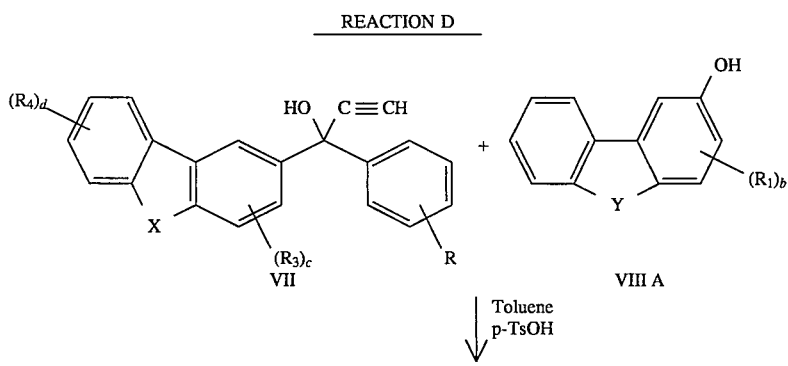

-continued
REACTION D

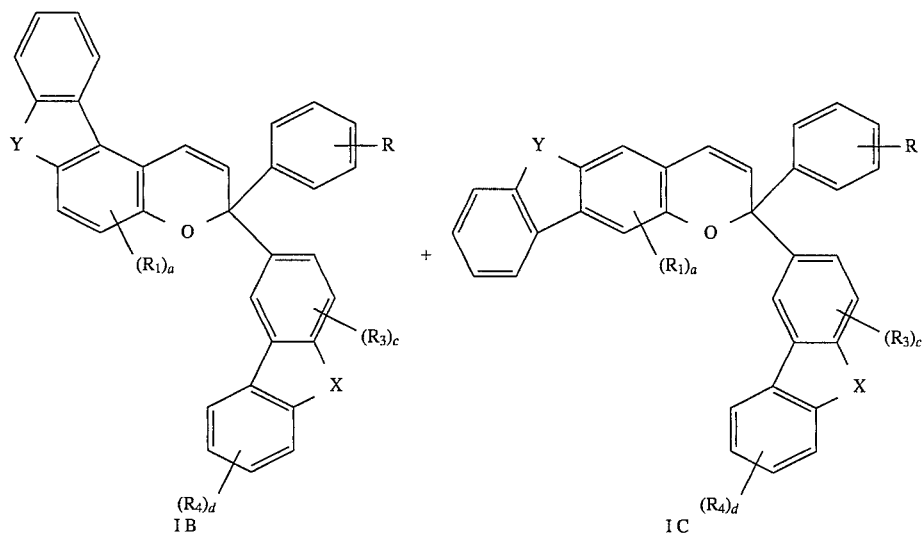

Hydroxydibenzofurans or hydroxydibenzothiophenes represented by the graphic formula VIII C, when not commercially available, can be prepared by different pathways. As shown in Reaction E and described in further detail in the Journal of the American Chemical Society, Volume 61, 1939, page 951 and Volume 62, 1940, pages 667 to 669, treatment of compounds represented by graphic formula VIII B with $_2$ equivalents of n-butyl lithium (2 n-BuLi) followed by reaction with an electrophile such as $CO_2$, $(CH_3)2NCHO$, haloalkyl, cyanoalkyl, cyanophenyl, cyanonaphthyl, $CH_3ONH_2$, trialkoxyboride, halogen etc... under acidic conditions ($H^+$) will produce $R_1$ substituents such as —COOH, —CHO, alkyl, alkylcarbonyl, phenylcarbonyl, naphthylcarbonyl, —$NH_2$, —OH, halogen etc.

REACTION E

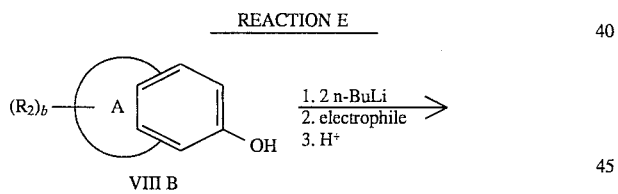

-continued
REACTION E

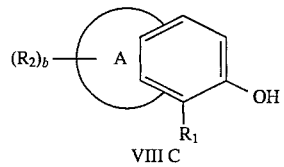

In Reaction F, benzothiophenes or benzofurans having fused benzo substituents, represented by graphic formulae X and XI, may be prepared from substituted or unsubstituted 2,2'-dihydroxybiphenyls represented by graphic formula IX. For further information on this reaction, see the Journal of the American Chemical Society, Volume 87(2), 1965, page 214.

REACTION F

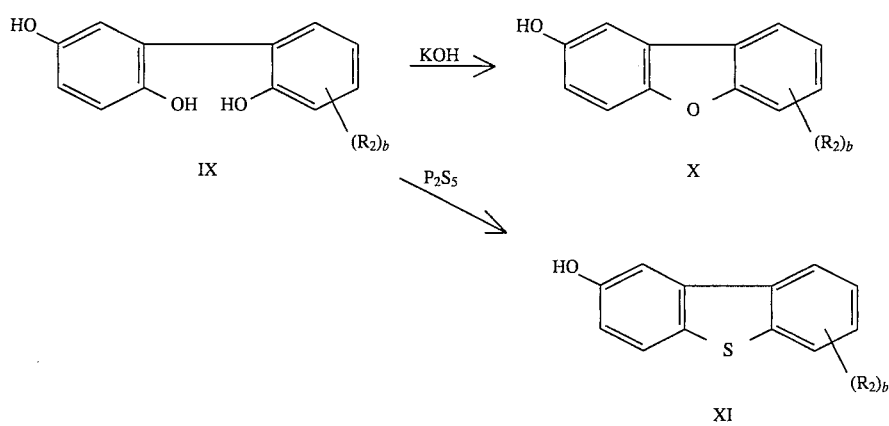

For further information on the synthesis of hydroxydibenzofurans or hydroxydibenzothiaphenes, see *Heterocyclic Compounds*, Robert C. Elderfield, 1951, Vol. 2, Chapter 3 (Dibenzofuran) and Chapter 5 (Dibenzothiophene); *The Chemistry of Heterocyclic Compounds*, H. D. Hartough and S. L. Meisel, 1954, Vol. 7, Chapter IV (Dibenzothiophene and its Derivatives); *Advances in Heterocyclic Chemistry*, A. R. Katritzky and A. J. Boulton, 1974, Vol. 16, Chapter V (Recent Advances in the Chemistry of Dibenzothiophenes); B. Akermark, H. Erdtman and C. A. Wachtmeister, *Acta Chemica Scandinavica*, Vol. 13, 1959, pages 1855–1862; S. Gronowitz, M. Herslof, R. Svenson, G. Bondesson and O. Magnusson, Acta Pharm. Suec., Vol. 15 1978, pages 337–360; and French Patent 816,719 issued Aug. 16, 1937. As described in these references, several different substituents may be attached to the compound of graphic formula VIII by using a combination of reactions.

Compounds represented by graphic formula I may be used in those applications in which organic photochromic substances may be employed, such as optical lenses, e.g., vision correcting ophthalmic and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. Benzopyrans represented by graphic formula I exhibit color changes from colorless to colors ranging from yellow to red/purple.

Examples of contemplated benzopyrans within the scope of the invention are the following:

(a) 3-phenyl-3-(dibenzofur-2-yl)-3H-naphtho[2, 1b]pyran;
(b) 3-phenyl-3-(dibenzofur-2-yl)-3H-benzo (b) furo[3,2-f]-1-benzopyran;
(c) 3-(dibenzofur-2-yl)-3-(2-methoxyphenyl)-3H-benzo (b) furo[3,2-f]-1-benzopyran;
(d) 3-(dibenzofur-2-yl)-3-(2-methoxyphenyl)-3H-benzo (b) thieno[3,2-f]-1-benzopyran;
(e) 3-(dibenzofur-2-yl)-3-(2-fluorophenyl)-3H-benzo (b) furo[3,2-f]-1-benzopyran;
(f) 2-(dibenzofur-2-yl)-2-(2-fluorophenyl)-11-formyl-3H-benzo (b) furo [2,3-g]-1-benzopyran
(g) 2-(9-ethylcarbazol-3-yl)-2-(4-methoxyphenyl)-5,8-dimethyl-2H-benzo (b) thieno[3,2-h]-1-benzopyran;
(h) 2-(dibenzothien-2-yl)-2-(4-methoxyphenyl)-5-methoxycarbonyl- 6-phenyl-2H-benzo (b) thieno[3,2-h]1-benopyran;
(i) 2-(dibenzofur-2-yl)-2-(4-morpholinophenyl)-2H-benzo (b) furo[3,2-h]-1-benzopyran; and
(j) 3-(9-phenylcarbazol-3-yl)-3-(4-methoxyphenyl)-2H-benzo (b) thieno[2,3-f]-1-benzopyran.

It is contemplated that the organic photochromic benzopyrans of graphic formulae I, I A, I B, and I C be used in combination with other appropriate complementary organic photochromic materials so that together they produce a near neutral gray or brown color shade when the plastic lens containing such photochromic materials are exposed to ultraviolet light. For example, a compound which colors to yellow may be blended with a compound that colors to an appropriate purple to produce a brown shade. Similarly, a compound which is orange in its colored state will produce a shade of gray when used in conjunction with an appropriate blue coloring compound. The aforesaid described combination of photochromic materials may be used also in applications other than ophthalmic lenses.

The novel benzopyran compounds of the present invention, such as those heretofore described, may be used alone or in combination with complementary photochromic compounds, i.e., organic photochromic compounds having at least one activated absorption maxima within the range of between about 400 and 700 nanometers, or substances containing same, and may be incorporated, e.g., dissolved or dispersed, in a polymeric organic host material used to prepare photochromic articles and which compounds or mixtures of compounds color when activated to an appropriate hue.

A first group of complementary organic photochromic substances-contemplated for use with the organic photochromic benzopyrans of the present invention are those having an activated absorption maximum within the visible range of greater than 570 nanometers, e.g., between about greater than 570 to 700 nanometers. These materials typically exhibit a blue, blueish-green, or blueish-purple color when exposed to ultraviolet light in an appropriate solvent or matrix. Many of such compounds are described in the open literature. For example, spiro(indoline)naphthoxazines have been described, among others, in U.S. Pat. Nos. 3,562,172; 3,578,602; 4,215,010; and 4,342,668; spiro(indoline)naphthoxazines having certain substituents on the 8' and 9' positions of the naphthoxazine portion of the molecule are described in U.S. Pat. No. 5,405,958; spiro(indoline)pyridobenzoxazines are described in U.S. Pat. No. 4,637,698; spiro(benzindoline)pyridobenzoxazines and spiro(benzindoline)naphthoxazines are described in U.S. Pat. 4,931,219; spiro(benzindoline)naphthopyrans are described in Japanese Patent Publication 62/195383; spiro(indoline)benzoxazines are described in U.S. Pat. No. 4,816,584; spiro(indoline)benzopyrans, spiro(indoline)naphthopyrans, and spiro(indoline-)quinopyrans are described, for example, in U.S. Pat. No. 4,880,667; and benzopyrans and naphthopyrans having a nitrogen-containing substituent in the 2-position of the pyran ring are described in U.S. Pat. No. 4,818,096. Spiro(indoline)pyrans are also described in the text, *Techniques in Chemistry*, Volume III, "Photochromism," Chapter 3, Glenn H. Brown, Editor, John Wiley and Sons, Inc., New York, 1971.

A second group of organic photochromic substances contemplated for use as complementary photochromic compounds are those having at least one absorption maximum and preferably two absorption maxima, within the visible range of between about 400 and less than 550 nanometers. These materials typically exhibit a yellow to red/purple color when exposed to ultraviolet light in an appropriate solvent or matrix. Such compounds include certain chromenes, i.e., benzopyrans and naphthopyrans. Many of such chromenes are described in the open literature, e.g., U.S. Pat. Nos. 3,567,605; 4,826,977; and 5,066,818. Other examples of complementary benzopyrans and naphthopyrans that may be used with the benzopyrans of the present invention include: those having a spiro adamantane group at the position alpha to the oxygen atom of the pyran ring, which are described in U.S. Pat. No. 4,826,977; benzopyrans having a substituted or unsubstituted benzothienyl or benzofuranyl and a substituted or unsubstituted phenyl at the 2 position of the pyran which are the subject of co-pending U.S. Pat. No. 5,429,774; 2H-naphtho-[1,2-b]pyran compounds having certain substitutents at the number 5 and 6 carbon atoms of the naphtho portion of the naphthopyran and at the 2 position of the pyran, which are the subject of co-pending U.S. patent application Ser. No. 8/164,187, filed Dec. 9, 1993; 3H-naphtho[2,1-b]pyrans having at least one ortho-substituted phenyl substituent at the 3-position of the pyran ring, which are described in U.S. Pat. No. 5,066,818; 3H-naphtho[2,1-b]pyran compounds having certain substituents at the number 8 carbon atom and certain substituents at the number 7 or 9 carbon atom, all substituents being on the naphtho portion of the naphthopyran, which are the subject of co-pending U.S. patent application Ser. No. 08/080,246, filed Jun. 21, 1993; 3H-naphtho[2,1b]pyrans substituted at the 3 position of the pyran ring with (i) an aryl substituent and (ii) a phenyl substituent having a 5- or 6-member heterocyclic ring fused at the number 3 and 4 carbon atoms of the phenyl substituent are described in U.S. Pat. No. 5,384,077; diaryl-3H-naphtho[2,1-b]pyran compounds having a substituted or unsubstituted, 5 or 6 member heterocyclic ring fused to the g, i, or 1 side of the naphthopyran which are the subject of co-pending U.S. patent application Ser. No.08/225,022 filed Apr. 8, 1994; naphthopyran compounds substituted at the number 8 carbon atom on the naphtho portion of the naphthopyran ring, with for example, a methoxy group which are the subject of U.S. Pat. No. 5,238,931; naphthopyran compounds, examples of which are 3-aryl- 3-arylalkenyl naphthopyrans, which are described in U.S. Pat. No. 5,274,132; and naphtho[2,1-b] pyrans substituted at the number five carbon atom with, for example, an acetoxy group, which are the subject of U.S. Pat. No. 5,244,602.

A third group of complementary organic photochromic substances contemplated for use with the organic photochromic benzopyrans of the present invention are those having an absorption maximum within the visible range of between about 400 to about 500 nanometers and another absorption maximum within the visible range of between about 500 to about 700 nanometers. These materials typically exhibit color(s) ranging from yellow to purple and yellow/brown to purple/gray when exposed to ultraviolet light in an appropriate solvent or matrix. Examples of these compounds include certain substituted 2H-phenanthro[4,3-b]pyrans; substituted 3H-phenanthro[1,2-b]pyrans; and benzopyran compounds, such as those having substituents at the 2-position of the pyran ring and a substituted or unsubstituted heterocyclic ring, such as a benzothieno or benzofurano ring fused to the benz portion of the benzopyran. Such later described compounds are the subject of co-pending U.S. patent application Nos. 08/286,039 filed Aug. 4, 1994 and U.S. Pat. No. 5,411,679.

Photochromic articles of the present invention may contain one photochromic compound or a mixture of photochromic compounds, as desired or required. Individual photochromic compounds or mixtures of photochromic compounds may be used to attain certain activated colors such as neutral grays or browns.

The compounds of the present invention (hereinafter also referred to and included as a second group photochromic compound) may be used also in combination with the organic photochromic substances of the first complementary group of photochromic compounds described herein, i.e., those that color to colors blue, blueish-green, or blueish-purple or with other organic photochromic substances in the aforesaid second group of photochromic compounds. Either members of the first or second group of photochromic compounds or mixtures of such compounds may be combined with or used in conjunction with the third group described herein that exhibit colors ranging from yellow to purple and yellow/brown to purple/gray.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds.

A neutral gray color exhibits a spectrum that has relatively equal absorption in the visible range between 400 and 700 nanometers. A neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, New York (1981). As used herein, a near neutral color is one in which the chromaticity coordinate values of "x" and "y" for the color are within the following ranges (D65 illuminant): x=0.260 to 0.400. y=0.280 to 0.400 following activation to 40 percent luminous transmission by exposure to solar radiation (Air Mass 1 or 2).

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from about 0.05 to about 1.0. e.g., from 0.1 to about 0.45, milligrams per square centimeter of surface to which the photochromic substance(s) is incorporated or applied. When mixtures of the aforedescribed organic photochromic complementary groups are used, the weight ratio of such materials, i.e., (first to second), (second to third), and (benzopyran of the present invention to other second group compounds) will vary from about 1:3 to about 3:1, e.g., between about 0.75:1 and about 2:1. The combination of the first, second, and third described organic photochromic complementary groups may have a weight ratio that will vary from about 1:3:1 to 3:1:3.

The photochromic substances of the present invention may be applied to or incorporated into a host material such as a polymeric organic host material by various methods described in the art. Such methods include dissolving or dispersing the photochromic substance within the host material, e.g., casting it in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; and applying the photochromic substance as part of a coating placed on the surface of the host material. The term "imbibition" or "imbibe" is intended to mean and include permeation of the photochromic substance alone into the host material, solvent assisted transfer of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

Adjuvant materials may also be incorporated into the host material with the photochromic substances prior to, simultaneously with or subsequent to application or incorporation of the photochromic substances in the host material. For example, ultraviolet light absorbers may be admixed with photochromic substances before their application to the host material or such absorbers may be superposed, e.g., superimposed, as a layer between the photochromic substance and the incident light. Further, stabilizers may be admixed with the photochromic substances prior to their application to the host material to improve the light fatigue resistance of the photochromic substances. Stabilizers, such as hindered amine light stabilizers and singlet oxygen quenchers, e.g., a nickel ion complex with an organic ligand, are contemplated. They may be used alone or in combination. Such stabilizers are described in U.S. Pat. No. 4,720.356. Finally, appropriate protective coating(s) may be applied to the surface of the host material. These may be abrasion resistant coatings and/or coatings that serve as oxygen barriers. Such coatings are known in the art.

The host material will usually be transparent, but may be translucent or even opaque. The host material need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Preferably, the host color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

Examples of polymeric organic host materials which may be used with the photochromic substances or compositions described herein include: polymers, i.e., homopolymers and copolymers, of polyol(allyl carbonate) monomers, diethylene glycol dimethacrylate monomers, diisopropenyl benzene monomers, and alkoxylated polyhydric alcohol acrylate monomers such as ethoxylated trimethylol propane triacrylate monomers; polymers, i.e., homopolymers and copolymers, of polyfunctional, i.e., mono-, di-, tri-, tetra, or multi-functional, acrylate and/or methacrylate monomers, polyacrylates, polymethacrylates, poly($C_1$–$C_{12}$ alkyl methacrylates) such as poly(methyl methacrylate), polyoxy(alkylene methacrylates) such as poly(ethylene glycol bis methacrylates), poly(alkoxylated phenol methacrylates) such as poly(ethoxylated bisphenol A dimethacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, polyesters, poly(ethylene terephthalate), polystyrene, poly (alpha methylstyrene), copoly(styrene-methyl methacrylate), copoly-(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis(allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. No. 4,360.653 and 4,994,208; and copolymers with aliphatic urethanes, the terminal portion of which contain allyl or acrylyl functional groups as described in U.S. Pat. No. 5,200.483; poly(vinyl acetate), polyvinylbutyral, polyurethane, polymers of members of the group consisting of diethylene glycol dimethacrylate monomers, diisopropenyl benzene monomers, and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile. More particularly, contemplated is use of the photochromic naphthopyrans of the present invention with optical organic resin monomers used to produce optically clear polymerizates, i.e., materials suitable for optical applications, such as for example plano and ophthalmic lenses, windows, and automotive transparencies. Such optically clear polymerizates may have a refractive index that may range from about 1.48 to about 1.75, e.g., from about 1.495 to about 1.66.

The present invention is more particularly described in the following examples which are intended as illustrative only, since numerous modifications and variations therein will be apparent to those skilled in the art.

EXAMPLE 1

STEP 1

Dibenzofuran (6 gram, 0.035 mole) and benzoyl chloride (0.038 mole) were added to a reaction flask containing 50 milliliters of anhydrous methylene chloride and stirred at room temperature. Anhydrous aluminum chloride (0.04 mole) was added slowly to the mixture. The reaction mixture was stirred one hour and then poured into a 5 weight percent aqueous hydrochloric acid and ice mixture. The resulting mixture was stirred 15 minutes and extracted with methylene chloride. The organic layer was separated and washed first with 10 weight percent aqueous sodium hydroxide followed by distilled water. The organic layer was separated and dried over anhydrous magnesium sulfate. The methylene chloride solvent was removed under vacuum. The resulting oily product crystallized from hexane. The recovered product, 9 grams, was filtered and air dried. A nuclear magnetic resonance (NMR) spectrum showed the desired product to have a structure consistent with 2-benzoyldibenzofuran.

STEP 2

2-Benzoyldibenzofuran, 9 grams from Step 1, was added to a reaction flask containing 100 milliliters of anhydrous tetrahydrofuran saturated with acetylene and stirred at room temperature under an argon atmosphere. An 18 weight percent suspension of sodium acetylide in xylene/mineral oil (a 10 percent molar excess of sodium acetylide) was added and the reaction mixture was stirred 6 hours at room temperature. The contents of the reaction flask was added to a 5 weight percent aqueous hydrochloric acid and ice mixture. The resulting mixture was extracted with diethyl ether. The organic layer was separated, washed, and dried over anhydrous sodium sulfate. The solvents were removed under vacuum to yield an oily product containing 1-phenyl-1-(dibenzofur-2-yl)-2-propyn-1-ol, which was not purified further but used directly in the next step.

STEP 3

2-Naphthol (5.0 grams, 0.035 mole) and all of the oily product containing 1-phenyl-1-(dibenzofur-2-yl)-2-propyn-1-ol from Step 2 were added to a reaction flask containing 200 milliliters of toluene and stirred at room temperature. A catalytic amount of p-toluenesulfonic acid (about 100 milligrams) was added and the mixture was stirred for about 6 hours. Afterwards, the reaction mixture was poured into water, the organic layer was separated and washed first with a 10 weight percent aqueous sodium hydroxide solution and then with water. The washed organic layer was dried over anhydrous sodium sulfate. The remaining solvent, toluene, was removed under vacuum. The resulting oil was purified using a silica gel column and a 1:3 mixture of chloroform:hexane as the eluant. The photochromic fractions were combined and the eluant was removed under vacuum. The resulting product was induced to crystallize from hexane. The recovered product, about 3.5 grams, had a melting point of 188° C. A nuclear magnetic resonance (NMR) spectrum showed the desired product to have a structure consistent with 3-phenyl-3-(dibenzofur-2-yl)- 3H-naphtho[2,1-b]pyran.

EXAMPLE 2

The process of Example 1 was followed except that in Step 3, 2-hydroxydibenzofuran (2.0 grams) was used in place of 2-naphthol. The recovered product, about 1.5 grams, was in the form of an oil. A nuclear magnetic resonance (NMR) spectrum showed the product to have a structure consistent with 3-phenyl-3-(dibenzofur-2-yl)-3H-benzo(b)furo[3,2-f]-1-benzopyran as the major product, and 2-phenyl-2-(dibenzofur-2-yl)- 2H-benzo(b)furo[2,3-g]-1-benzopyran, as the minor product. The product containing both major and minor isomers was used for further testing.

EXAMPLE 3

The process of Example 1 was followed except that in Step 1, 2-methoxybenzoylchloride was used in place of benzoylchloride to produce 2-(2-methoxybenzoyl)-dibenzofuran; in Step 2, 2-(2-methoxybenzoyl)-dibenzofuran was used in place of 2-benzoyldibenzofuran to produce 1-(2-methoxyphenyl)-1-(dibenzofur- 2-yl)-2-propyn-1-ol; and in Step 3,1-(2-methoxyphenyl)- 1-(dibenzofur-2-yl)-2-propyn-1-ol was used in place of 1-phenyl-1-(dibenzofur-2-yl)-2-propyn-1-ol and 2-hydroxydibenzofuran was used in place of 2-naphthol. The recovered product, about 1.8 grams, had a melting point of 210° to 215° C. A nuclear magnetic resonance (NMR) spectrum showed the product to have a structure consistent with 3-(2-methoxyphenyl)- 3-(dibenzofur-2-yl)-3H-benzo(b)furo[3,2-f]-1-benzopyran as the major product, and 2-(2-methoxyphenyl)-2-(dibenzofur- 2-yl)-2H-benzo(b)furo[2,3-g]-1-benzopyran, as the minor product. The product containing both major and minor isomers was used for further testing.

EXAMPLE 4

The procedure of Step 3 of Example 1 was followed except that. 2-hydroxydibenzothiophene (2.0 gram) was used in place of 2-naphthol and 1-(2-methoxyphenyl)-1-(dibenzofur-2-yl)- 2-propyn-1-ol (3.0 gram) was used in place of 2-naphthol and 1-(2-naphthol and 1-(2-methoxyphenyl)-1-(dibenzofur-2-yl)-2-propyn-1-ol. The recovered product, about 1.5 grams, was in the form of an oil. A nuclear magnetic resonance (NMR) spectrum showed the product to have a structure consistent with 3-(2-methoxyphenyl)-3-(dibenzofur-2-yl)-3H-benzo(b)thieno[3,2-f]-1-benzopyran as the major product and 2-(2-methoxyphenyl)-2-(dibenzofur-2-yl)-2H-benzo(b)thieno[2,3-g]-1-benzopyran as the minor product. The product containing both major and minor isomers was used for further testing.

EXAMPLE 5

The process of Example 1 was followed except that in Step 1, 2-fluorobenzoylchloride was used in place of benzoylchloride to produce 2-(2-fluorobenzoyl)-dibenzofuran; in Step 2, 2-(2-fluorobenzoyl)-dibenzofuran was used in place of 2-benzoyldibenzofuran to produce 1-(2-fluorophenyl)-1-(dibenzofur- 2-yl)-2-propyn-1-ol; and in Step 3, 1(2-fluorophenyl)- 1-(dibenzofur-2-yl)-2-propyn-1-ol was used in place of 1-phenyl-1-(dibenzofur-2-yl)-2-propyn-1-ol and 2-hydroxydibenzofuran was used in place of 2-naphthol. The recovered product, about 1.5 grams, was in the form of an oil. A nuclear magnetic resonance (NMR) spectrum showed the product to have a structure consistent with 3-(2-fluorophenyl)- 3-(dibenzofur-2-yl)-3H-benzo(b)furo[3,2-f]-1-benzopyran as the major product, and 2-(2-fluorophenyl)-2-(dibenzofur- 2-yl)-2H-benzo(b)furo[2,3-g]-1-benzopyran, as the minor product. The product containing both major and minor isomers was used for further testing.

EXAMPLE 6

Step 1

2-Hydroxydibenzofuran (10.0 grams, 0.054 mole) was added to a reaction flask containing about 200 ml of tetrahydrofuran under an argon atmosphere and stirred. n-Butyl lithium, 70 ml of a 1.6 molar solution, was added dropwise to the flask, and the contents were heated to 60° C, and stirred for 14 to 16 hours. The reaction mixture was cooled to room temperature and a solution of dimethylformamide, 4.5 grams in 10 ml of diethyl ether, was added dropwise and the reaction mixture was stirred for 48 hours. Afterwards, the resulting mixture was dissolved in 5 weight percent aqueous hydrochloric acid solution and extracted with three 50 ml portions of diethyl ether. The organic extracts were combined, washed with distilled water, and dried over magnesium sulfate. The solvent, diethyl ether, was removed under vacuum to yield a yellow oily product. The recovered product, about 8.0 grams, was crystallized from a 1:1 mixture of diethyl ether:hexane. A nuclear magnetic resonance (NMR) spectrum showed the product to have a structure consistent with 1-formyl-2-hydroxydibenzofuran.

Step 2

The process of Example 1 was followed except that in Step 1, 2-fluorobenzoylchloride was used in place of benzoylchloride to produce 2-(2-fluorobenzoyl)-dibenzofuran; in Step 2, 2-(2-fluorobenzoyl)-dibenzofuran was used in place of 2-benzoyldibenzofuran to produce 1-(2-fluorophenyl)-1-(dibenzofur- 2-yl)-2-propyn-1-ol; and in Step 3, 1-(2-fluorophenyl)-1-(dibenzofur-2-yl)- 2-propyn-1-ol was used in place of 1-phenyl-1-(dibenzofur-2-yl)-2-propyn-1-ol and 1-formyl-2-hydroxydibenzofuran was used in place of 2-naphthol. The recovered product, about 1.2 grams, was in the form of an oil. A nuclear magnetic resonance (NMR) spectrum showed the product to have a structure consistent with 2-(dibenzofur-2-yl)-2-(2-fluorophenyl)-11-formyl-2H-benzo(b)furo[2,3-g]-1-benzopyran.

EXAMPLE 7

Part A

The benzopyrans prepared in the Examples were incorporated into an ethyl cellulose resin by the following procedure. About 30 milligrams of the photochromic compound was added to 2.0 grams of a 10 weight percent ethyl cellulose solution in toluene. The benzopyran compound was dissolved by warming and stirring on a steam bath. Approximately 2.0 grams of the resultant solution was deposited on the edge of a 75 by 25 millimeter (mm) glass slide. Using a draw down bar, a 0.2 mm layer of photochromic resin solution was placed evenly on the slide and permitted to dry.

Part B

The photochromic test samples prepared in Part A were tested for photochromic response rates on an optical bench. Prior to testing on the optical bench, the photochromic test samples were exposed to 365 nanometer (nm) ultraviolet light for about 15 minutes to activate the photochromic compounds and then placed into a 76° C. oven for about 15 minutes to bleach or inactivate the photochromic compounds. The test samples were then cooled to room temperature, exposed to fluorescent room lighting for at least 2 hours and then kept covered for at least 2 hours prior to testing on an optical bench maintained at 75° F. (23.9° C.).

The optical bench comprises a 150 watt Xenon arc lamp, a tungsten lamp, power supplies for both lamps, condensing lenses as needed to maintain collimated light beams from both lamps, a remote controlled shutter, a copper sulfate bath acting as a heat sink for the arc lamp, a Schott WG-320 nm cut-off filter which removes short wavelength radiation, neutral density filter(s), a sample holder in which the sample to be tested is inserted, a photopic filter, light detector, and radiometer assembly, a strip chart recorder, and a means for maintaining the alignment of the aforestated components during testing.

Change in optical density ($\Delta$ OD) of a sample was determined by inserting a photochromic test sample in the bleached state into the sample holder, adjusting the transmittance scale to 100%, opening the shutter from the Xenon lamp to provide ultraviolet radiation to change the sample from the bleached state to an activated (darkened) state, measuring the transmittance through the sample. The transmittance was measured by directing a beam of light from the tungsten lamp at a small angle normal to the surface of the sample, through the sample, and to a photopic filter, light detector and radiometer assembly. The photopic filter passes wavelengths such that the detector mimics the response of the human eye and produces output signals that are processed by the radiometer. The change in optical density was calculated according to the formula $\Delta$ OD=log(100/% Ta) where %Ta is the percent transmittance in the activated state and the logarithm is to the base 10.

The $\Delta$ OD/Min, which represents the sensitivity of the photochromic compound's response to UV light, was measured over the first five (5) seconds of UV exposure, then expressed on a per minute basis. The saturation optical density (OD) was taken under identical conditions as the $\Delta$ OD/Min, except UV exposure was continued for 15 minutes. The lambda max value, which is the maximum absorption of the activated (colored) form of the photochromic compound in ethyl cellulose resin, may occur at one or two wavelengths reported as Band A and Band B in Table 1. The Bleach Rate T ½ is the time interval in seconds for the absorbance of the activated form of the benzopyran in the test sample to reach one half the highest absorbance at room temperature (72° F., 22.2° C.) after removal of the source of activating light. Results are tabulated in Table 1.

TABLE 1

| COMPOUND EXAMPLE | LAMBDA MAX | | SENSITIVITY | OD | BLEACH RATE |
| --- | --- | --- | --- | --- | --- |
| | BAND A | BAND B | $\Delta$OD/MIN | @ SAT | T ½(SEC.) |
| 1 | 439 | — | 0.69 | 0.32 | 61 |
| 2 | 444 | 524 | 0.27 | 0.20 | 245 |
| 3 | 448 | 510 | 0.47 | 0.97 | 800 |
| 4 | 452 | 502 | 0.46 | 0.54 | 451 |
| 5 | 446 | 528 | 0.31 | 0.41 | 508 |
| 6 | 416 | 442 | 0.20 | 0.25 | 406 |

The results of Table 1 for the Example compounds of the present invention demonstrate the effects of each compound having a different substituent on the parameters tested, such as, visible spectra, i.e., lambda max; fade rate, i.e., bleach rate; activated intensity, i.e., OD at saturation; and coloration rate, i.e., sensitivity.

Although the present invention has been described with reference to the specific details of particular embodiments thereof, it is not intended that such details be regarded as limitations upon the scope of the invention except insofar as to the extent that they are included in the accompanying claims.

I claim:

1. A benzopyran compound represented by the following graphic formula:

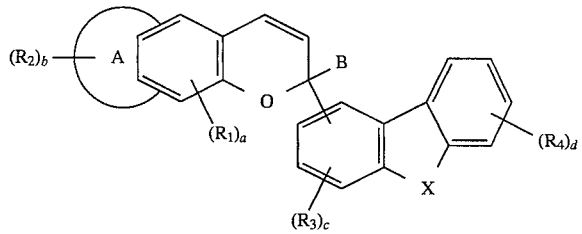

wherein, (a) X is $CH_2$, O, S, or N—$R_{12}$, wherein $R_{12}$ is selected from the group consisting of hydrogen, $C_1$–$C_6$ alkyl, $C_5$–$C_7$ cycloalkyl, unsubstituted, mono- and di-substituted phenyl, said phenyl substituents being $C_1$–$C_6$ alkyl, $C_1$–$C_6$ alkoxy, chloro, or fluoro, $R_3$ and $R_4$ are each hydrogen, $C_1$–$C_6$ alkyl, $C_1$–$C_6$ alkoxy, chloro or fluoro, and c and d are each the integers 0, 1, 2, or 3;

(b) each $R_1$ is selected from the group consisting of halogen, $C_1$–$C_6$ alkyl, $C_3$–$C_7$ cycloalkyl, the unsubstituted, mono-, and di-substituted aryl groups phenyl and naphthyl, and the groups, —C(O)W, —N($R_5$)$R_6$, and —O$R_7$, wherein W is hydrogen, $C_1$–$C_6$ alkoxy, or —N($R_5$)$R_6$, $R_5$ and $R_6$ are each selected from the group consisting of hydrogen, $C_1$–$C_6$ alkyl, $C_5$–$C_7$ cycloalkyl, unsubstituted, mono- and di-substituted phenyl, or $R_5$ and $R_6$ together with the nitrogen atom form an unsubstituted, mono-, or di-substituted heterocyclic ring selected from the group consisting of 1-indolinyl, morpholino, piperidino, and 1-pyrrolidyl, $R_7$ is hydrogen, $C_1$–$C_6$ alkyl, unsubstituted or mono-substituted phenyl($C_1$–$C_3$)alkyl, $C_1$–$C_6$ alkoxy($C_2$–$C_4$)alkyl, $C_3$–$C_7$ cycloalkyl, mono($C_1$–$C_4$)alkyl substituted($C_3$–$C_7$)cycloalkyl, $C_1$–$C_6$ haloalkyl, allyl, or the group, —C(O)Y, wherein Y is $C_1$–$C_6$ alkyl, $C_1$–$C_6$ alkoxy, the unsubstituted, mono-, or di-substituted aryl groups phenyl or naphthyl, an unsubstituted, mono-, or di-substituted phenoxy, $C_1$–$C_6$ alkylamino, an unsubstituted, mono-, or di-substituted phenylamino, each of said heterocyclic, phenyl, naphthyl, phenyl($C_1$–$C_3$)alkyl, phenoxy, and phenylamino substituents being $C_1$–$C_6$ alkyl or $C_1$–$C_6$ alkoxy, each of said halogen or halo substituents being chloro or fluoro, and a is the integer 0, 1, or 2;

(c) A is selected from the group consisting of benzothieno, benzofurano, and benzo, the 2,3 or 3,2 position of said benzothieno or benzofurano group being fused to the f, g, or h side of said benzopyran compound, said benzo group being fused to the f side of said benzopyran compound, and each $R_2$ is selected from the group consisting of $R_1$ and an unsubstituted, mono-, or di-substituted benzo group fused to the benzo portion of the benzothieno or benzofurano of group A, said benzo substituents being $C_1$–$C_4$ alkyl, $C_1$–$C_4$ alkoxy, $C_5$–$C_7$ cycloalkyl, chloro or fluoro, and b is the integer 0, 1, or 2, provided that when $R_2$ is an unsubstituted, mono-, or di-substituted benzo group, b is 1;

(d) B is selected from the group consisting of:

(i) the unsubstituted, mono-, di-, and tri-substituted aryl groups phenyl and naphthyl;

(ii) the unsubstituted, mono-, and di-substituted heterocyclic aromatic groups pyridyl, furanyl, benzofuran-2-yl, benzofuran-3-yl, thienyl, benzothien-2-yl, and benzothien-3-yl, said phenyl, naphthyl, and heterocyclic substituents being selected from the group consisting of —N($R_5$)$R_6$, hydroxy, $C_1$–$C_6$ alkyl, $C_1$–$C_6$ haloalkyl, $C_1$–$C_6$ alkoxy, mono($C_1$–$C_6$)alkoxy($C_1$–$C_4$)alkyl, acryloxy, methacryloxy and halogen, said halogen or (halo) groups being fluoro or chloro;

(iii) the groups represented by the following graphic formulae:

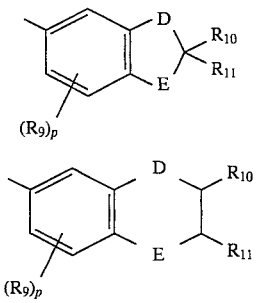

wherein D is carbon or oxygen, and E is oxygen or substituted nitrogen provided that when E is substituted nitrogen, D is carbon, said nitrogen substituents being selected from the group consisting of hydrogen, $C_1$–$C_6$ alkyl, $C_2$–$C_6$ acyl, and $C_1$–$C_5$ alkylcarbonyl; $R_{10}$ and $R_{11}$ are each hydrogen or $C_1$–$C_6$ alkyl; each $R_9$ is $C_1$–$C_6$ alkyl, $C_1$–$C_6$ alkoxy, hydroxy or halogen, said halogen being chloro or fluoro; and p is the integer 0, 1, or 2;

(iv) $C_1$–$C_6$ alkyl, $C_1$–$C_6$ haloalkyl, ($C_1$–$C_6$)alkoxy($C_1$–$C_4$)alkyl, $C_3$–$C_6$ cycloalkyl, mono($C_1$–$C_6$)alkoxy($C_3$–$C_6$)cycloalkyl, and halo($C_3$–$C_6$)cycloalkyl, each of said halo groups being fluorine or chlorine; and (v) the group represented by the following graphic formula:

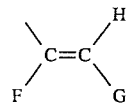

wherein F is hydrogen or $C_1$–$C_4$ alkyl, and G is selected from the unsubstituted, mono-, and di-substituted members of the group consisting of naphthyl, phenyl, furanyl, and thienyl, said group substituents being $C_1$–$C_4$ alkyl, $C_1$–$C_4$ alkoxy, fluoro, or chloro.

2. The benzopyran of claim 1 wherein, (a) X is O, S, or N—$R_{12}$, wherein $R_{12}$ is selected from the group consisting of hydrogen, $C_1$–$C_4$ alkyl, $C_5$–$C_7$ cycloalkyl, unsubstituted, mono- and di-substituted phenyl, said phenyl substituents being $C_1$–$C_4$ alkyl, $C_1$–$C_4$ alkoxy, chloro, or fluoro, $R_3$ and $R_4$ are each hydrogen, $C_1$–$C_4$ alkyl, $C_1$–$C_4$ alkoxy, chloro or fluoro, and c and d are each the integers 0, 1, 2, or 3;

(b) each $R_1$ is selected from the group consisting of fluoro, $C_1-C_4$ alkyl, $C_5-C_7$ cycloalkyl, unsubstituted, mono-, and di-substituted phenyl, the groups —C(O)W, —N($R_5$)$R_6$, and —O$R_7$, wherein W is hydrogen, $C_1-C_4$ alkoxy, or —N($R_5$)$R_6$, $R_5$ and $R_6$ are each selected from the group consisting of hydrogen, $C_1-C_4$ alkyl, $C_5-C_7$ cycloalkyl, unsubstituted, and mono-substituted phenyl, or $R_5$ and $R_6$ together with the nitrogen atom form an unsubstituted or mono-substituted heterocyclic ring selected from the group consisting of 1-indolinyl, morpholino, piperidino, and 1-pyrrolidyl, $R_7$ is hydrogen, $C_1-C_4$ alkyl, an unsubstituted or mono-substituted phenyl($C_1-C_2$)alkyl, $C_1-C_4$alkoxy($C_2-C_4$)alkyl, $C_5-C_7$ cycloalkyl, mono($C_1-C_2$)alkyl substituted ($C_3-C_7$) cycloalkyl, $C_1-C_4$ haloalkyl, allyl, or the group, —C(O)Y, wherein Y is $C_1-C_4$alkyl or $C_1-C_4$ alkoxy, each of said heterocyclic, phenyl and Phenyl($C_1-C_2$)alkyl substituents being $C_1-C_4$ alkyl or $C_1-C_4$ alkoxy, and a is 0, 1, or 2;

(c) A is selected from the group consisting of benzothieno, benzofurano, and benzo, the 2,3 or 3,2 position of said benzothieno or benzofurano group being fused to the f or g side of said benzopyran compound, said benzo group being fused to the f side of said benzopyran compound, each $R_2$ is selected from the group consisting of $R_1$, an unsubstituted, mono-, or di-substituted benzo group fused to the benzo portion of the benzothieno or benzofurano of group A, said benzo substituents being $C_1-C_3$ alkyl, $C_1-C_3$ alkoxy, $C_5-C_6$ cycloalkyl, or fluoro, and b is 0, 1, or 2, provided that when $R_2$ is an unsubstituted, mono-, or di-substituted benzo group, b is 1;

(d) B is selected from the group consisting of:
 (i) unsubstituted, mono-, di-, and tri-substituted phenyl;
 (ii) the unsubstituted, mono- and di-substituted heterocyclic aromatic groups pyridyl, furanyl, benzofuran-2-yl, benzofuran-3-yl, thienyl, benzothien-2-yl, and benzothien-3-yl, said phenyl and heterocyclic substituents being selected from the group consisting of —N($R_5$)$R_6$, hydroxy, $C_1-C_4$ alkyl, $C_1-C_4$ haloalkyl, $C_1-C_4$ alkoxy, and halogen, said halogen or (halo) groups being fluoro or chloro;
 (iii) the group represented by the following graphic formulae:

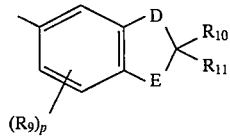

wherein D is carbon and E is oxygen; $R_{10}$ and $R_{11}$ are each hydrogen or $C_1-C_4$ alkyl; each $R_9$ is $C_1-C_4$ alkyl, $C_1-C_4$ alkoxy, hydroxy or halogen, said halogen being chloro or fluoro; and p is the integer 0, 1, or 2;
 (iv) $C_1-C_4$ alkyl, $C_1-C_6$ alkoxy($C_1-C_4$)alkyl, and $C_3-C_6$ cycloalkyl; and
 (v) the group represented by the following graphic formula:

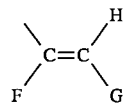

wherein F is hydrogen or methyl, and G is phenyl or mono-substituted phenyl, said phenyl substituents being $C_1-C_4$ alkyl, $C_1-C_4$ alkoxy, or fluoro.

3. The benzopyran of claim 2 wherein,
(a) X is O, S, or N—$R_{12}$, wherein $R_{12}$ is $C_1-C_4$ alkyl, $R_3$ and $R_4$ are each hydrogen, $C_1-C_3$ alkyl, $C_1-C_3$ alkoxy, or fluoro, and c and d are each 0, 1 or 2;
(b) each $R_1$ is selected the group consisting of fluoro, $C_1-C_3$ alkyl, phenyl, and the groups —C(O)W, —N($R_5$)$R_6$, and —O$R_7$, wherein W is hydrogen, $C_1-C_3$ alkoxy, or —N($R_5$)$R_6$, $R_5$ and $R_6$ are each selected from the group consisting of hydrogen, $C_1-C_3$ alkyl, $C_5-C_7$ cycloalkyl, unsubstituted, and mono-substituted phenyl, or $R_5$ and $R_6$ form an unsubstituted or mono-substituted heterocyclic ring selected from the group consisting of 1-indolinyl, morpholino, and piperidino, $R_7$ is hydrogen, $C_1-C_3$ alkyl or the group, —C(O)Y, wherein Y is $C_1-C_3$ alkyl or $C_1-C_3$ alkoxy, each of said phenyl and heterocyclic substituents being $C_1-C_2$ alkyl or $C_1-C_2$ alkoxy, and a is 0 or 1;
(c) A is selected from the group consisting of benzothieno, benzofurano, and benzo, the 2,3 or 3,2 position of said benzothieno or benzofurano group being fused to the f or g side of said benzopyran compound, said benzo group being fused to the f side of said benzopyran compound, each $R_2$ is selected from the group consisting of $R_1$, an unsubstituted, or mono-substituted benzo group fused to the benzo portion of the benzothieno or benzofurano of group A, said benzo substituents being $C_1-C_2$ alkyl, $C_1-C_2$ alkoxy, or fluoro, and b is 0 or 1, provided that when $R_2$ is an unsubstituted, mono-, or di-substituted benzo group, b is 1;
(d) B is selected from the group consisting of:
 (i) unsubstituted, mono-, and di-substituted phenyl;
 (ii) the unsubstituted, mono- and di-substituted heterocyclic aromatic groups pyridyl, furanyl, benzofuran-2-yl, thienyl, and benzothien-2-yl, said phenyl and heterocyclic substituents being selected from the group consisting of —N($R_5$)$R_6$, hydroxy, $C_1-C_3$ alkyl, $C_1-C_3$ alkoxy, and fluoro; and
 (iii) the group represented by the following graphic formulae:

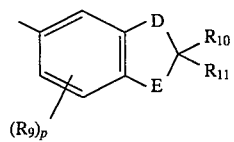

wherein D is carbon and E is oxygen; $R_{10}$ and $R_{11}$ are each hydrogen or $C_1-C_2$ alkyl; each $R_9$ is $C_1-C_3$ alkyl, $C_1-C_3$ alkoxy, or fluoro; and p is the integer 0, 1, or 2.

4. The benzopyran of claim 3 wherein,
(a) X is O, S, or N—$R_{12}$, wherein $R_{12}$ is $C_1-C_2$ alkyl, $R_3$ and $R_4$ are each hydrogen, $C_1-C_2$ alkyl, $C_1-C_2$ alkoxy, or fluoro, and c and d are each 0 or 1;
(b) each $R_1$ is $C_1-C_2$ alkyl, phenyl, the group —C(O)W, or —O$R_7$, wherein W is hydrogen or $C_1-C_2$ alkoxy, $R_7$ is hydrogen, $C_1-C_2$ alkyl, or the group, —C(O)Y, wherein Y is $C_1-C_2$ alkyl or $C_1-C_2$ alkoxy, and a is 0 or 1;
(c) A is selected from the group consisting of benzothieno, benzofurano, and benzo, the 3,2 position of said benzothieno or benzofurano group being fused to the f or g side of said benzopyran compound, said benzo group being fused to the f side of said benzopyran compound, each $R_2$ is $R_1$ or a benzo group fused to the benzo portion of the benzothieno or benzofurano of group A, and b is 0 or 1, provided that when $R_2$ is an unsubstituted, mono-, or di-substituted benzo group, b is 1;

(d) B is selected from the group consisting of:
(i) unsubstituted, mono-, and di-substituted phenyl;
(ii) the unsubstituted, mono- and di-substituted heterocyclic aromatic groups pyridyl, furanyl, benzofuran-2-yl, thienyl, and benzothien-2-yl, said phenyl and heterocyclic substituents being selected from the group consisting of morpholino, $C_1$–$C_2$ alkyl, $C_1$–$C_2$ alkoxy, and fluoro; and
(iii) the group represented by the following graphic formulae:

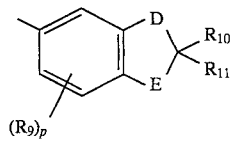

wherein D is carbon and E is oxygen; $R_{10}$ and $R_{11}$ are each hydrogen or $C_1$–$C_2$ alkyl; each $R_9$ is $C_1$–$C_2$ alkyl, $C_1$–$C_2$ alkoxy, or fluoro; and p is the integer 0 or 1.

5. A benzopyran selected from the group consisting of:
(a) 3-phenyl-3-(dibenzofur-2-yl)-3-H-naphtho[2,1-b]pyran;
(b) 3-phenyl-3-(dibenzofur-2-yl)-3H-benzo(b)furo[3,2-f]-1-benzopyran;
(c) 3-(dibenzofur-2-yl)-3-(2-methoxyphenyl)-3H-benzo(b)furo[3,2-f]-1-benzopyran;
(d) 3-(dibenzofur-2-yl)-3-(2-methoxyphenyl)-3H-benzo(b)thieno[3,2-f]-1-benzopyran;
(e) 3-(dibenzofur-2-yl)-3-(2-fluorophenyl)-3H-benzo(b)furo[3,2-f]-1-benzopyran;
(f) 2-(dibenzofur-2-yl)-2-(2-fluorophenyl)-11-formyl-3H-benzo(b)furo[2,3-g]-1-benzopyran
(g) 2-(9-ethylcarbazol-3-yl)-2-(4-methoxyphenyl)-5,8-dimethyl-2H-benzo(b)thieno[3,2-h]-1-benzopyran;
(h) 2-(dibenzothien-2-yl)-2-(4-methoxyphenyl)-5-methoxycarbonyl-6-phenyl-2H-benzo(b)thieno[3,2-h]-1-benzopyran;
(i) 2-(dibenzofur-2-yl)-2-(4-morpholinophenyl)-2-H-benzo(b)furo[3,2-h]-1-benzopyran; and
(j) 3-(9-phenylcarbazol-3-yl)-3-( 4-methoxyphenyl)-2H-benzo(b)thieno[2,3-f]-1-benzopyran.

6. A photochromic article comprising a polymeric organic host material and a photochromic amount of a benzopyran compound of claim 1.

7. The photochromic article of claim 6 wherein the polymeric organic host material is selected from the group consisting of polyacrylates, polymethacrylates, poly($C_1$–$C_{12}$ alkyl methacrylates), polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

8. A photochromic article comprising a polymeric organic host material and a photochromic amount of a benzopyran compound of claim 2.

9. The photochromic article of claim 8 wherein the polymeric organic host material is selected from the group consisting of polyacrylates, polymethacrylates, poly($C_1$–$C_{12}$ alkyl methacrylates), polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

10. The photochromic article of claim 9 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis-(allyl carbonate) monomers, diethylene glycol dimethacrylate monomers, diisopropenyl benzene monomers, and ethoxylated trimethylol propane triacrylate monomers.

11. The photochromic article of claim 10 wherein the photochromic compound is present in an amount of from about 0.05 to 1.0 milligram per square centimeter of organic host material surface to which the photochromic substance(s) is incorporated or applied.

12. The photochromic article of claim 11 wherein the article is a lens.

13. A photochromic article comprising a photochromic amount of the benzopyran compound of claim 3 and a polymeric organic host material selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis-(allyl carbonate) monomers, diethylene glycol dimethacrylate monomers, diisopropenyl benzene monomers, and ethoxylated trimethylol propane triacrylate monomers.

14. A photochromic article comprising a photochromic amount of the benzopyran compound of claim 4 and a polymeric organic host material selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis-(allyl carbonate) monomers, diethylene glycol dimethacrylate monomers, diisopropenyl benzene monomers, and ethoxylated trimethylol propane triacrylate monomers.

15. A photochromic article comprising, in combination, a solid transparent polymeric organic host material, and a photochromic amount of each of (a) at least one benzopyran compound of claim 1, and (b) at least one other organic photochromic compound having at least one activated absorption maxima within the range of between about 400 and 700 nanometers.

16. The photochromic article of claim 15 wherein the polymeric organic host material is selected from the group consisting of polyacrylates, polymethacrylates, poly($C_1$–$C_{12}$ alkyl methacrylates), polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styreneacrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

17. The photochromic article of claim 15 wherein the organic photochromic compound (b) is selected from the group consisting of:

(i) organic photochromic substances having at least one absorption maximum in the visible range of between 400 and less than 550 nanometers;

(ii) organic photochromic substances having absorption maxima within the visible range of between about 400 and about 500 nanometers and between about 500 and about 700 nanometers;

(iii) organic photochromic substances having an activated absorption maximum in the visible range of greater than 570 nanometers; and (iv) mixtures of said organic photochromic substances.

18. The photochromic article of claim 17 wherein the organic photochromic compound (b) is an organic photochromic substances having an activated absorption maxima in the visible range of greater than 570 nanometers.

19. The photochromic article of claim 16 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis-(allyl carbonate) monomers, diethylene glycol dimethacrylate monomers, diisopropenyl benzene monomers, and ethoxylated trimethylol propane triacrylate monomers.

20. The photochromic article of claim 17 wherein the organic photochromic compound (b) is selected from the group consisting of spiro(indoline)naphthoxazines, spiro(indoline)pyridobenzoxazines, spiro(benzindoline)pyridobenzoxazines, spiro(benzindoline)naphthoxazines, spiro(benzindoline)naphthopyrans, spiro(indoline)benzoxazines, spiro(indoline)benzopyrans, spiro(indoline)naphthopyrans, spiro(indoline)quinopyrans, spiro(indoline)pyrans, 3H-naphtho[2,1-b]pyrans, 2H-phenanthro[4,3-b]pyrans; 3H-phenanthro[1,2-b]pyrans; benzopyran compounds and mixtures of such photochromic substances.

* * * * *